(12) United States Patent
Burnie et al.

(10) Patent No.: US 7,132,512 B2
(45) Date of Patent: Nov. 7, 2006

(54) MEDICAMENT FOR THE TREATMENT OF CHLAMYDIAL INFECTION

(75) Inventors: James Peter Burnie, Alderley Edge (GB); Ruth Christine Matthews, Alderley Edge (GB)

(73) Assignee: NeuTec Pharma PLC, Manchester (GB)

( * ) Notice: Subject to any disclaimer, the term of this patent is extended or adjusted under 35 U.S.C. 154(b) by 302 days.

(21) Appl. No.: 10/634,914

(22) Filed: Aug. 6, 2003

(65) Prior Publication Data

US 2004/0029806 A1 Feb. 12, 2004

Related U.S. Application Data

(63) Continuation of application No. 09/889,314, filed as application No. PCT/GB00/00237 on Jan. 28, 2000, now abandoned.

(30) Foreign Application Priority Data

Feb. 5, 1999 (GB) ................................ 9902555.3

(51) Int. Cl.
*C07K 16/18* (2006.01)
*C07K 14/47* (2006.01)
*A61K 38/17* (2006.01)

(52) U.S. Cl. ................ 530/388.1; 530/350; 424/234.1; 424/263.1; 424/190.1; 424/192.1; 435/69.1; 435/69.7; 536/23.4; 536/23.1

(58) Field of Classification Search ............. 424/234.1, 424/263.1, 190.1, 192.1; 435/69.7, 69.1; 536/23.4, 23.1; 530/350, 388.1

See application file for complete search history.

(56) References Cited

U.S. PATENT DOCUMENTS 6,165,478 A * 12/2000 Izutsu et al. ............. 424/263.1

FOREIGN PATENT DOCUMENTS

| JP | 0784059 | 7/1997 |
| WO | WO 96/09320 | 3/1996 |
| WO | WO 99/27105 | 6/1999 |

OTHER PUBLICATIONS

Accession No. AAR94585, AAR94579, AAR94586 or AAWO 1743.*
Kalman et al. "Comparative genomes of Chlamydia pneumoniae and *C. trachomatis*" Nature Genetics. vol. 21 (Apr. 1999) pp. 385-389 (XP002141432).
Kornak et al. "Sequence analysis of the gene encoding the *Chlamydia pneumoniae* Dnak protein homolog" Infection and Immunity, US, American Society for Microbiology 59:2 (1991) pp. 721-725 (XP002076846).
Kanamoto et al. "Antigenic characterization of *Chlamydia pneumoniae* isolated in Hiroshima, Japan" Microbiology and Immunology, 37:6 (Jan. 1993) pp. 495-498 (XP002088968).
Iijima et al. "Characterization of *Chlamydia pneumoniae* species-specific proteins immunodominant in humans" Journal of Clinical Microbiology, 32:3 (Mar. 1994) pp. 583-588 (XP002115816).
Perez Melgosa et al. "Isolation and characterization of a gene encoding a *Chlamydia pneumoniae* 76-kilodalton protein containing a species-specific epitope" Infection and Immunity, 62:3 (1994) pp. 880-886 (XP002076845).

* cited by examiner

*Primary Examiner*—Lynette R. Smith
*Assistant Examiner*—Padma Baskar
(74) *Attorney, Agent, or Firm*—Jones Day

(57) ABSTRACT

The present invention concerns treatment, prevention and diagnosis of infection due to *Chlamydia pneumoniae* and, in particular, to the prevention and treatment of atherosclerosis, including coronary atherosclerosis, caused by same.

2 Claims, No Drawings

SEQUENCE LISTING

<160> NUMBER OF SEQ ID NOS: 16

<210> SEQ ID NO 1
<211> LENGTH: 1491
<212> TYPE: DNA
<213> ORGANISM: Chlamydia pneumoniae
<220> FEATURE:
<221> NAME/KEY: CDS
<222> LOCATION: (1)..(1491)

<400> SEQUENCE: 1

```
gat aca aac atg tct att tca tct tct tca gga cct gac aat caa aaa      48
Asp Thr Asn Met Ser Ile Ser Ser Ser Ser Gly Pro Asp Asn Gln Lys
  1               5                  10                  15 aat atc atg tct caa gtt ctg aca tcg aca ccc cag ggc gtg ccc caa      96
Asn Ile Met Ser Gln Val Leu Thr Ser Thr Pro Gln Gly Val Pro Gln
             20                  25                  30 caa gat aag ctg tct ggc aac gaa acg aag caa ata cag caa aca cgt     144
Gln Asp Lys Leu Ser Gly Asn Glu Thr Lys Gln Ile Gln Gln Thr Arg
         35                  40                  45 cag ggt aaa aac act gag atg gaa agc gat gcc act att gct ggt gct     192
Gln Gly Lys Asn Thr Glu Met Glu Ser Asp Ala Thr Ile Ala Gly Ala
     50                  55                  60 tct gga aaa gac aaa act tcc tcg act aca aaa aca gaa aca gct cca     240
Ser Gly Lys Asp Lys Thr Ser Ser Thr Thr Lys Thr Glu Thr Ala Pro
 65                  70                  75                  80 caa cag gga gtt gct gct ggg aaa gaa tcc tca gaa agt caa aag gca     288
Gln Gln Gly Val Ala Ala Gly Lys Glu Ser Ser Glu Ser Gln Lys Ala
                 85                  90                  95 ggt gct gat act gga gta tca gga gcg gct gct act aca gca tca aat     336
Gly Ala Asp Thr Gly Val Ser Gly Ala Ala Ala Thr Thr Ala Ser Asn
            100                 105                 110 act gca aca aaa att gct atg cag acc tct att gaa gag gcg agc aaa     384
Thr Ala Thr Lys Ile Ala Met Gln Thr Ser Ile Glu Glu Ala Ser Lys
        115                 120                 125 agt atg gag tct acc tta gag tca ctt caa agc ctc agt gcc gcg caa     432
Ser Met Glu Ser Thr Leu Glu Ser Leu Gln Ser Leu Ser Ala Ala Gln
    130                 135                 140 atg aaa gaa gtc gaa gcg gtt gtt gtt gct gcc ctc tca ggg aaa agt     480
Met Lys Glu Val Glu Ala Val Val Val Ala Ala Leu Ser Gly Lys Ser
145                 150                 155                 160 tcg ggt tcc gca aaa ttg gaa aca cct gag ctc ccc aag ccc ggg gtg     528
Ser Gly Ser Ala Lys Leu Glu Thr Pro Glu Leu Pro Lys Pro Gly Val
                165                 170                 175 aca cca aga tca gag gtt atc gaa atc gga ctc gcg ctt gct aaa gca     576
Thr Pro Arg Ser Glu Val Ile Glu Ile Gly Leu Ala Leu Ala Lys Ala
            180                 185                 190 att cag aca ttg gga gaa gcc aca aaa tct gcc tta tct aac tat gca     624
Ile Gln Thr Leu Gly Glu Ala Thr Lys Ser Ala Leu Ser Asn Tyr Ala
        195                 200                 205 agt aca caa gca caa gca gac caa aca aat aaa cta ggt cta gaa aag     672
Ser Thr Gln Ala Gln Ala Asp Gln Thr Asn Lys Leu Gly Leu Glu Lys
    210                 215                 220 caa gcg ata aaa atc gat aaa gaa cga gaa gaa tac caa gag atg aag     720
Gln Ala Ile Lys Ile Asp Lys Glu Arg Glu Glu Tyr Gln Glu Met Lys
225                 230                 235                 240 gct gcc gaa cag aag tct aaa gat ctc gaa gga aca atg gat act gtc     768
Ala Ala Glu Gln Lys Ser Lys Asp Leu Glu Gly Thr Met Asp Thr Val
                245                 250                 255
```

-continued

| | | |
|---|---|---|
| aat act gtg atg atc gcg gtt tct gtt gcc att aca gtt att tct att<br>Asn Thr Val Met Ile Ala Val Ser Val Ala Ile Thr Val Ile Ser Ile<br>          260                 265              270 | | 816 |
| gtt gct gct att ttt aca tgc gga gct gga ctc gct gga ctc gct gcg<br>Val Ala Ala Ile Phe Thr Cys Gly Ala Gly Leu Ala Gly Leu Ala Ala<br>        275                 280             285 | | 864 |
| gga gct gct gta ggt gca gcg gca gct gga ggt gca gca gga gct gct<br>Gly Ala Ala Val Gly Ala Ala Ala Ala Gly Gly Ala Ala Gly Ala Ala<br>290                 295                300 | | 912 |
| gcc gca acc acg gta gca aca caa att aca gtt caa gct gtt gtc caa<br>Ala Ala Thr Thr Val Ala Thr Gln Ile Thr Val Gln Ala Val Val Gln<br>305                 310               315             320 | | 960 |
| gcg gtg aaa caa gct gtt atc aca gct gtc aga caa gcg atc acc gcg<br>Ala Val Lys Gln Ala Val Ile Thr Ala Val Arg Gln Ala Ile Thr Ala<br>               325               330             335 | | 1008 |
| gct ata aaa gcg gct gtc aaa tct gga ata aaa gca ttt atc aaa act<br>Ala Ile Lys Ala Ala Val Lys Ser Gly Ile Lys Ala Phe Ile Lys Thr<br>               340               345             350 | | 1056 |
| tta gtc aaa gcg att gcc aaa gcc att tct aaa gga atc tct aag gtt<br>Leu Val Lys Ala Ile Ala Lys Ala Ile Ser Lys Gly Ile Ser Lys Val<br>          355                 360             365 | | 1104 |
| ttc gct aag gga act caa atg att gcg aag aac ttc ccc aag ctc tcg<br>Phe Ala Lys Gly Thr Gln Met Ile Ala Lys Asn Phe Pro Lys Leu Ser<br>370                 375                380 | | 1152 |
| aaa gtc atc tcg tct ctt acc agt aaa tgg gtc acg gtt ggg gtt ggg<br>Lys Val Ile Ser Ser Leu Thr Ser Lys Trp Val Thr Val Gly Val Gly<br>385                 390               395             400 | | 1200 |
| gtt gta gtt gcg gcg cct gct ctc ggt aaa ggg att atg caa atg cag<br>Val Val Val Ala Ala Pro Ala Leu Gly Lys Gly Ile Met Gln Met Gln<br>                    405               410             415 | | 1248 |
| ctc tcg gag atg caa caa aac gtc gct caa ttt cag aaa gaa gtc gga<br>Leu Ser Glu Met Gln Gln Asn Val Ala Gln Phe Gln Lys Glu Val Gly<br>               420               425             430 | | 1296 |
| aaa ctg cag gct gcg gct gat atg att tct atg ttc act caa ttt tgg<br>Lys Leu Gln Ala Ala Ala Asp Met Ile Ser Met Phe Thr Gln Phe Trp<br>          435                 440             445 | | 1344 |
| caa cag gca agt aaa att gcc tca aaa caa aca ggc gag tct aat gaa<br>Gln Gln Ala Ser Lys Ile Ala Ser Lys Gln Thr Gly Glu Ser Asn Glu<br>450                 455               460 | | 1392 |
| atg act caa aaa gct acc aag ctg ggc gct caa atc ctt aaa gcg tat<br>Met Thr Gln Lys Ala Thr Lys Leu Gly Ala Gln Ile Leu Lys Ala Tyr<br>465                 470               475             480 | | 1440 |
| gcc gca atc agc gga gcc atc gct ggc gca cat aaa acc aat aat ttt<br>Ala Ala Ile Ser Gly Ala Ile Ala Gly Ala His Lys Thr Asn Asn Phe<br>                    485               490             495 | | 1488 |
| taa | | 1491 |

<210> SEQ ID NO 2
<211> LENGTH: 496
<212> TYPE: PRT
<213> ORGANISM: Chlamydia pneumoniae

<400> SEQUENCE: 2

Asp Thr Asn Met Ser Ile Ser Ser Ser Gly Pro Asp Asn Gln Lys
1               5                   10                  15

Asn Ile Met Ser Gln Val Leu Thr Ser Thr Pro Gln Gly Val Pro Gln
            20                  25                  30

Gln Asp Lys Leu Ser Gly Asn Glu Thr Lys Gln Ile Gln Gln Thr Arg
        35                  40                  45

```
Gln Gly Lys Asn Thr Glu Met Glu Ser Asp Ala Thr Ile Ala Gly Ala
     50                  55                  60

Ser Gly Lys Asp Lys Thr Ser Ser Thr Thr Lys Thr Glu Thr Ala Pro
 65                  70                  75                  80

Gln Gln Gly Val Ala Ala Gly Lys Glu Ser Ser Glu Ser Gln Lys Ala
                     85                  90                  95

Gly Ala Asp Thr Gly Val Ser Gly Ala Ala Thr Thr Ala Ser Asn
                100                 105                 110

Thr Ala Thr Lys Ile Ala Met Gln Thr Ser Ile Glu Glu Ala Ser Lys
            115                 120                 125

Ser Met Glu Ser Thr Leu Glu Ser Leu Gln Ser Leu Ser Ala Ala Gln
    130                 135                 140

Met Lys Glu Val Glu Ala Val Val Ala Ala Leu Ser Gly Lys Ser
145                 150                 155                 160

Ser Gly Ser Ala Lys Leu Glu Thr Pro Glu Leu Pro Lys Pro Gly Val
                165                 170                 175

Thr Pro Arg Ser Glu Val Ile Glu Ile Gly Leu Ala Leu Ala Lys Ala
            180                 185                 190

Ile Gln Thr Leu Gly Glu Ala Thr Lys Ser Ala Leu Ser Asn Tyr Ala
            195                 200                 205

Ser Thr Gln Ala Gln Ala Asp Gln Thr Asn Lys Leu Gly Leu Glu Lys
    210                 215                 220

Gln Ala Ile Lys Ile Asp Lys Glu Arg Glu Glu Tyr Gln Glu Met Lys
225                 230                 235                 240

Ala Ala Glu Gln Lys Ser Lys Asp Leu Glu Gly Thr Met Asp Thr Val
                245                 250                 255

Asn Thr Val Met Ile Ala Val Ser Val Ala Ile Thr Val Ile Ser Ile
                260                 265                 270

Val Ala Ala Ile Phe Thr Cys Gly Ala Gly Leu Ala Gly Leu Ala Ala
            275                 280                 285

Gly Ala Ala Val Gly Ala Ala Ala Gly Gly Ala Ala Gly Ala Ala
    290                 295                 300

Ala Ala Thr Thr Val Ala Thr Gln Ile Thr Val Gln Ala Val Val Gln
305                 310                 315                 320

Ala Val Lys Gln Ala Val Ile Thr Ala Val Arg Gln Ala Ile Thr Ala
                325                 330                 335

Ala Ile Lys Ala Ala Val Lys Ser Gly Ile Lys Ala Phe Ile Lys Thr
            340                 345                 350

Leu Val Lys Ala Ile Ala Lys Ala Ile Ser Lys Gly Ile Ser Lys Val
            355                 360                 365

Phe Ala Lys Gly Thr Gln Met Ile Ala Lys Asn Phe Pro Lys Leu Ser
370                 375                 380

Lys Val Ile Ser Ser Leu Thr Ser Lys Trp Val Thr Val Gly Val Gly
385                 390                 395                 400

Val Val Val Ala Ala Pro Ala Leu Gly Lys Gly Ile Met Gln Met Gln
                405                 410                 415

Leu Ser Glu Met Gln Gln Asn Val Ala Gln Phe Gln Lys Glu Val Gly
                420                 425                 430

Lys Leu Gln Ala Ala Ala Asp Met Ile Ser Met Phe Thr Gln Phe Trp
            435                 440                 445

Gln Gln Ala Ser Lys Ile Ala Ser Lys Gln Thr Gly Glu Ser Asn Glu
    450                 455                 460

Met Thr Gln Lys Ala Thr Lys Leu Gly Ala Gln Ile Leu Lys Ala Tyr
```

```
                465                 470                 475                 480
Ala Ala Ile Ser Gly Ala Ile Ala Gly Ala His Lys Thr Asn Asn Phe
                    485                 490                 495

<210> SEQ ID NO 3
<211> LENGTH: 302
<212> TYPE: PRT
<213> ORGANISM: Artificial Sequence
<220> FEATURE:
<223> OTHER INFORMATION: Description of Artificial Sequence: Codon
      optimised N-terminal section of Chlamydia
      pneumoniae protein
<221> NAME/KEY: UNSURE
<222> LOCATION: (1)..(30)
<223> OTHER INFORMATION: S-tag and thrombin cleavage site
<220> FEATURE:
<223> OTHER INFORMATION: Positions (297)..(302) comprise Histidine tag

<400> SEQUENCE: 3

Met Lys Glu Thr Ala Ala Ala Lys Phe Glu Arg Gln His Met Asp Ser
  1               5                  10                  15

Pro Asp Leu Gly Thr Leu Val Pro Arg Gly Ser Ala Ile Ser Asp Pro
                 20                  25                  30

Asp Thr Asn Met Ser Ile Ser Ser Ser Gly Pro Asp Asn Gln Lys
             35                  40                  45

Asn Ile Met Ser Gln Val Leu Thr Ser Thr Pro Gln Gly Val Pro Gln
 50                  55                  60

Gln Asp Lys Leu Ser Gly Asn Glu Thr Lys Gln Ile Gln Gln Thr Arg
 65                  70                  75                  80

Gln Gly Lys Asn Thr Glu Met Glu Ser Asp Ala Thr Ile Ala Gly Ala
                 85                  90                  95

Ser Gly Lys Asp Lys Thr Ser Ser Thr Thr Lys Thr Glu Thr Ala Pro
                100                 105                 110

Gln Gln Gly Val Ala Ala Gly Lys Glu Ser Ser Glu Ser Gln Lys Ala
            115                 120                 125

Gly Ala Asp Thr Gly Val Ser Gly Ala Ala Ala Thr Thr Ala Ser Asn
        130                 135                 140

Thr Ala Thr Lys Ile Ala Met Gln Thr Ser Ile Glu Glu Ala Ser Lys
145                 150                 155                 160

Ser Met Glu Ser Thr Leu Glu Ser Leu Gln Ser Leu Ser Ala Ala Gln
                165                 170                 175

Met Lys Glu Val Glu Ala Val Val Ala Ala Leu Ser Gly Lys Ser
                180                 185                 190

Ser Gly Ser Ala Lys Leu Glu Thr Pro Glu Leu Pro Lys Pro Gly Val
            195                 200                 205

Thr Pro Arg Ser Glu Val Ile Glu Ile Gly Leu Ala Leu Ala Lys Ala
        210                 215                 220

Ile Gln Thr Leu Gly Glu Ala Thr Lys Ser Ala Leu Ser Asn Tyr Ala
225                 230                 235                 240

Ser Thr Gln Ala Gln Ala Asp Gln Thr Asn Lys Leu Gly Leu Glu Lys
                245                 250                 255

Gln Ala Ile Lys Ile Asp Lys Glu Arg Glu Glu Tyr Gln Glu Met Lys
                260                 265                 270

Ala Ala Glu Gln Lys Ser Lys Asp Leu Glu Gly Thr Met Asp Thr Val
            275                 280                 285

Asn Thr Val Ala Ala Ala Leu Glu His His His His His His
        290                 295                 300
```

```
<210> SEQ ID NO 4
<211> LENGTH: 9
<212> TYPE: PRT
<213> ORGANISM: Chlamydia pneumoniae

<400> SEQUENCE: 4

Ser Ala Lys Leu Glu Thr Pro Glu Leu
 1               5

<210> SEQ ID NO 5
<211> LENGTH: 7
<212> TYPE: PRT
<213> ORGANISM: Chlamydia pneumoniae

<400> SEQUENCE: 5

Pro Lys Pro Gly Val Thr Pro
 1               5

<210> SEQ ID NO 6
<211> LENGTH: 9
<212> TYPE: PRT
<213> ORGANISM: Chlamydia pneumoniae

<400> SEQUENCE: 6

Gly Val Thr Pro Arg Ser Glu Val Ile
 1               5

<210> SEQ ID NO 7
<211> LENGTH: 6
<212> TYPE: PRT
<213> ORGANISM: Chlamydia pneumoniae

<400> SEQUENCE: 7

Glu Val Ile Glu Ile Gly
 1               5

<210> SEQ ID NO 8
<211> LENGTH: 8
<212> TYPE: PRT
<213> ORGANISM: Chlamydia pneumoniae

<400> SEQUENCE: 8

Ala Ile Lys Ile Asp Lys Glu Arg
 1               5

<210> SEQ ID NO 9
<211> LENGTH: 6
<212> TYPE: PRT
<213> ORGANISM: Chlamydia pneumoniae

<400> SEQUENCE: 9

Ser Gly Pro Asp Asn Gln
 1               5

<210> SEQ ID NO 10
<211> LENGTH: 9
<212> TYPE: PRT
<213> ORGANISM: Chlamydia pneumoniae

<400> SEQUENCE: 10

Ser Gly Asn Glu Thr Lys Gln Ile Gln
 1               5

<210> SEQ ID NO 11
```

```
-continued

<211> LENGTH: 9
<212> TYPE: PRT
<213> ORGANISM: Chlamydia pneumoniae

<400> SEQUENCE: 11

Ser Glu Gly Gln Lys Ala Gly Ala Asp
 1               5

<210> SEQ ID NO 12
<211> LENGTH: 9
<212> TYPE: PRT
<213> ORGANISM: Chlamydia pneumoniae

<400> SEQUENCE: 12

Thr Ala Ile Glu Glu Ala Ser Lys Ser
 1               5

<210> SEQ ID NO 13
<211> LENGTH: 9
<212> TYPE: PRT
<213> ORGANISM: Chlamydia pneumoniae

<400> SEQUENCE: 13

Ser Lys Ser Met Glu Ser Thr Leu Glu
 1               5

<210> SEQ ID NO 14
<211> LENGTH: 9
<212> TYPE: PRT
<213> ORGANISM: Chlamydia pneumoniae

<400> SEQUENCE: 14

Glu Tyr Gln Glu Met Lys Ala Ala Glu
 1               5

<210> SEQ ID NO 15
<211> LENGTH: 14
<212> TYPE: PRT
<213> ORGANISM: Chlamydia pneumoniae

<400> SEQUENCE: 15

Glu Lys Gln Ala Ile Lys Ile Asp Lys Glu Arg Glu Glu Tyr
 1               5                  10

<210> SEQ ID NO 16
<211> LENGTH: 14
<212> TYPE: PRT
<213> ORGANISM: Chlamydia pneumoniae

<400> SEQUENCE: 16

Glu Thr Pro Glu Leu Pro Lys Pro Gly Val Thr Pro Arg Ser
 1               5                  10
```

MEDICAMENT FOR THE TREATMENT OF CHLAMYDIAL INFECTION

This application is a continuation of U.S. Ser. No. 09/889,314, filed Nov. 20, 2001, now abandoned, which is the national phase of International Application No. PCT/GB00/00237, filed Jan. 28, 2000, which designated the United States. These applications, in their entirety, are incorporated by reference.

The present invention concerns treatment, prevention and diagnosis of infection due to *Chlamydia pneumoniae* and in particular to the prevention and treatment of atherosclerosis, including coronary atherosclerosis, caused by same.

*C. pneumoniae* is associated with atherosclerosis but no definitive link between the two has yet been established (Hammerschlag, M. R., 1998, Eur. J. Clin. Microbiol. Infect. Dis., 17: 305–308). Friedank, H. M. et al. (1993, Eur. J. Clin. Microbiol. Infect. Dis., 12(12): 947–951) identify a 54 kDa *C. pneumoniae* antigen which was recognised by 93% of sera positive for *C. pneumoniae*, the antigen appearing to be located on the surface of elementary bodies. Wiedman, A. A. M. et al. (1997, Clin. Diagn. Labs. Immunol., 4(6):700–704) showed the infectivity of *C. pneumoniae* elementary bodies to be slightly reduced by the use of antibody specific against a 54 kDa *C. pneumoniae* protein.

Despite investigating it, other researchers have not confirmed the immunogenicity of the *C. pneumoniae* 54 kDa band (see for example Kutlin, A. and Roblin, P. M., 1998, J. Infect. Dis., 177: 720–724; Campbell, L. A. et al., 1990, J. Clin. Microbiol., 28(6): 1261–1264; Campbell, L. A. et al., 1990. Infection and Immunity, 58(1): 93–97; Puolakkainen, M. et al., 1993, J. Clin. Microbiol., 31(8): 2212–2214; hkima, Y. et al., 1994, J. Clin. Microbiol., 32(3): 583–588; Maass, M. and Gieffers, J., 1997, J. Infection, 35: 171–176; Gonen, R. et al., 1993, APMIS, 101:719–726).

The present inventor has now succeeded in isolating, purifying and identifying a *C. pneumoniae* protein which (together with inhibitors of same, such as antibodies) is protective and therapeutic against *C. pneumoniae* infection. The therapeutic role of the protein has previously neither been suggested nor disclosed.

According to the present invention there is provided a *C. pneumoniae* protein having the amino acid sequence of SEQ ID NO: 2, for use in a method of treatment or diagnosis of the human or animal body. The amino acid sequence has been confirmed by N-terminal amino-acid sequencing (see "Experimental" below) and the protein has a theoretical molecular weight of 50.8 kDa, although post-translational modifications such as glycosylation may of course affect its apparent molecular weight as determined by e.g. SDS-PAGE. Experiments (below) have shown it to have an apparent molecular weight of 51 kDa on SDS-PAGE gels.

As can be seen from the plethora of publications above, although some identify immunogenic bands at molecular weights of 50–54 kDa, no specific therapeutically effective proteins have been identified.

Experiments (below) have allowed the present inventor to isolate and purify the protein of the present invention and identify the gene sequence coding for the protein. This has allowed the determination of the protein amino acid sequence (above). The nucleotide sequence coding for same forms another part of the present invention. Thus according to the present invention there is also provided a nucleotide sequence coding for a protein according to the present invention, for use in a method of treatment or diagnosis of the human or animal body. Such a nucleotide sequence may have the sequence of SEQ ID NO: 1. Modified nucleotide sequences having codons encoding the same amino acid sequence will be readily apparent to one skilled in the art.

The nucleotide sequence of the present invention and the amino acid sequence it encodes are already known from the *Chlamydia* Genome Project (*C. pneumoniae* CWL029/CPn0809), as is an apparent *C. trachomatis* homologue (CT578). However, therapeutic and diagnostic uses for same have not been previously suggested.

The invention also extends to encompass forms of the protein which have been insubstantially modified (i.e. which have been partially modified), particularly forms of the protein which display the same immunogenic properties as the protein itself.

By "partial modification" and "partially modified" is meant, with reference to amino acid sequences, a partially modified form of the molecule which retains substantially the properties of the molecule from which it is derived, although it may of course have additional functionality. Partial modification may, for example, be by way of addition, deletion or substitution of amino acid residues. Substitutions may be conserved substitutions. Hence the partially modified molecule may be a homologue of the molecules from which it was derived. It may, for example, have at least 70% homology with the molecule from which it was derived. It may for example have at least 80, 90 or 95% homology with the molecule from which it was derived. An example of a homologue is an allelic mutant.

Also provided according to the present invention is the use of a protein, immunogenic fragment thereof or nucleic acid sequence encoding same according to the present invention in the manufacture of a medicament for the treatment of infection due to *C. pneumoniae*.

Immunogenic fragments of the protein include any fragment of the protein which elicits an immune response, and includes epitopes. Analogues (mimotopes) of epitopes may be readily created, the mimotopes having different sequences but displaying the same epitope and thus the term "immunogenic fragments" also encompasses immunogenic analogues of the fragments e.g. mimotopes. Epitopes may be readily determined and mimotopes readily designed (Geysen, H. M. et al., 1987, Journal of Immunological Methods, 102: 259–274; Geysen, H. M. et al.1988, J. Mol. Recognit., 1(1):32–41; Jung, G. and Beck-Sickinger, A. G., 1992, Angew. Chem. Int. Ed. Eng., 31: 367–486). Such an immunogenic fragment carrying epitopes may also be described as being a peptide having the amino acid sequence of the immunogenic fragment and which carries an epitope.

The present inventor has succeeded in isolating a number of epitopes (immunogenic fragments) of the protein of the present invention. Thus according to the present invention there is also provided an epitope having the amino acid sequence of any one of SEQ ID NOs: 4–14. In particular, SEQ ID NOs: 5–7 provide an overlapping set of highly immunogenic peptides—as can be seen from the experimental data (below) SEQ ID NO: 5 provides for especially good results. Similarly, excellent results are also obtained from SEQ ID NO: 8.

The protein, immunogenic fragments thereof and nucleic acid sequences encoding same may be used in therapy, both prophylactically (e.g. as immunostimulants such as vaccines) and for treatment of infection due to *C. pneumoniae*. For example a nucleotide sequence encoding the protein or immunogenic fragment thereof may be used in the manufacture of a DNA vaccine (Montgomery, D. L. et al., 1997, Pharmacol. Ther., 74(2): 195–205; Donnelly, J. J. et al., 1997, Annu. Rev. Immunol., 15: 617–648; Manickan, E. et al., 1997, Crit. Rev. Immunol., 17(2): 139–154).

Binding agents and inhibitors (such as antibodies or other neutralising agents) specific against the protein and immunogenic fragments thereof may also be used both diagnostically and therapeutically. Binding agents have a target to which they are specific, and in the case of a binding agent being an antibody, the target is an antigen. An example of a therapeutic medicament is antibody specific against the protein of the present invention, and this may be employed in immunotherapy, for example passive immunotherapy. Antibodies, their manufacture and use are well known (Harlow, E. and Lane, D., "Using Antibodies—A Laboratory Manual", Cold Spring Harbor Laboratory Press, New York, 1998) and so antibodies and antigen binding fragments thereof will be readily apparent to one skilled in the art, and reference herein to antibodies is also reference to antigen binding fragments unless stated otherwise. Other inhibitors such as ribozymes, antisense oligonucleotides and DNA vaccines will be readily apparent to one skilled in the art (Fries, P. C., 1999, "DNA Vaccines", New England Journal of medicine, 341: 1623–1624; Leitner, W. W. et al., 1999, "DNA and RNA based vaccines: principles, progress and prospects", Vaccine, 18: 765–777; Muotri, A. R. et al., 1999, "Ribozymes and the anti-gene therapy: how a catalytic RNA can be used to inhibit gene function", Gene, 237: 303–310; Rossi, J. J., 1999, "Ribozymes, genomics and therapeutics", Chemistry & Biology, 6: R33–R37; James, H. A., 1999, "The potential application of ribozymes for the treatment of haematological disorders", Journal of Leukocyte Biolofy, 66: 361–368)

Thus the present invention also provides the use of a inhibitor specific to the protein of the present invention in the manufacture of a medicament for the treatment of infection due to *C. pneumoniae*.

Also provided according to the present invention is a method of manufacture of a medicament for the treatment of infection due to *C. pneumoniae*, characterised in the use of a protein, immunogenic fragment or inhibitor according to the present invention.

Also provided according to the present invention is a method of treatment of infection due to *C. pneumoniae* (e.g. of a patient in need of same), comprising the step of administering to a patient a medicament comprising a protein immunogenic fragment or inhibitor according to the present invention. The exact dose of medicament administered to a patient may be readily determined using simple dose-response assays. Medicaments may additionally comprise a pharmaceutically acceptable carrier, diluent or excipient (Remington's Pharmaceutical Sciences and US Pharmacopeia, 1984, Mack Publishing Company, Easton, Pa., USA)

It has not been previously suggested that the protein of the present invention (or immunogenic fragments of same) is diagnostic for infection due to *C. pneumonia*. Binding agents specific to the protein of the present invention (for example antibodies) may also be used diagnostically, for example in an ELISA-type test. Thus also provided according to the present invention is the use of a protein, immunogenic fragment or binding agent according to the present invention in the manufacture of a diagnostic test for *C. pneumoniae*.

Also provided is a diagnostic test method for infection due to *C. pneumoniae* comprising the steps of:
  I) reacting an antibody specific against the protein of the present invention with serum from a patient;
  ii) detecting an antibody-antigen binding reaction; and
  iii) correlating the detection of an antibody-antigen binding reaction with the presence of the protein.

Such test methods may also be performed using other binding agents specific to the protein of the present invention.

Also provided is a kit of parts for performing such a test, characterised in that it comprises antibody specific against the protein of the present invention.

The invention will be further apparent from the following description, with reference to the several figures of the accompanying drawings, which show, by way of example only, uses of the proteins of the present invention.

EXPERIMENTAL

The experiments below detail the identification of a number of peptides and antisera against same which are useful in the therapy and diagnosis of infections due to *Chlamydia pneumoniae*. Starting with sera from infected patients, blotting against clinical isolates of *Chlamydia pneumoniae* showed the presence of an immunodominant antigen with an apparent molecular weight of 51 kDa, the antigen being stable to and released by octylglucoside treatment. N-terminal amino acid sequencing of the protein of the 51 kDa band allowed sequence database probing, in turn identifying a *C. pneumoniae* protein and a *C. trachomatis* homologue. Epitope mapping allowed the identification of antigenic peptides, which together with antibody against them were tested for their therapeutic and diagnostic efficacy.

Western Blotting—Using the Novex nuPAGE Electrophoresis System.

1. SDS Page

Preparation of Sample:

1. 100 μl of Novex SDS Sample loading buffer was added to 400 μl of a preparation of a *Chlamydia pneumoniae* clinical isolate and the mixture placed into a boiling waterbath for 10 minutes.
2. 10 μl of the mixture was loaded into each well of a Novex 4–12% Bis-Tris NuPage gel (1.0 mm, 12 well). In addition, 4 μl of Novex Multimark molecular weight standards were added to a single well on each gel.
3. Electrophoresis was performed using 1× Novex MOPS electrophoresis buffer at 200v for 40 minutes.

Western Transfer Protocol:

1. The blotting apparatus and the gel membrane "sandwiches" were assembled according to the protocol described in the Novex instruction booklet provided with the gels.
2. Blotting was performed using 1× Novex Transfer buffer containing 20% methanol. Transfer was carried out at 30v (constant) for 1 hour.
3. Following transfer, the membranes were removed from the apparatus and left to "Block" overnight in 3% Bovine Serum Albumin (BSA) at 4° C.

Probing With Patient's Serum:

1. The membranes were cut into strips and placed into the wells of incubation trays. Patients' serum was diluted 1 in 20 in 3% BSA and 2 ml added to each strip. (2 strips per patient).
2. The membranes were incubated at room temperature for 2 hours with agitation.
3. The strips were washed 5 times over 30 minutes with 0.85% NaCl/0.01% Tween 20.
4. 2 ml of goat anti-human IgM or IgG alkaline phosphatase conjugated anti-immunoglobulin diluted 1 in 4000 in 3%

BSA were added to each strip. The strips were incubated for a further hour at room temperature with agitation.
5. The membranes were washed a further 5 times as previously described.
6. Antibody-antigen interaction was visualised by the addition of NBT/BCIP (50 mg/ml) in pH 9.5 phosphate buffer.
7. The reaction was allowed to proceed until the bands had reached the required intensity.

Sera

Group A: Children with respiratory tract infection and no evidence of *Chlamydia pneumoniae* as shown by negative microimmunofluorescence (less than 1 in 64) test (n=19).

Group B: Children with respiratory tract infection and a microimmunofluorescence titre greater than 1 in 512 (n=18).

Group C: Patients undergoing cardiac surgery for advanced coronary disease (n=32). Ten of these had antibody on immunoblot.

Group D: Adults with respiratory tract infection and a *chlamydia* complement fixation test greater than 1 in 40 (n=27) using LGV 2 as an antigen.

Group E: Adults with pelvic inflammatory disease due to *Chlamydia trachomatis* (n=21).

Group F: Sera (n=11) which were positive for the 60/62 kDa doublet and band at 51 kDa were retested on antigen prepared from *Chlamydia pneumoniae* where the purified elementary bodies were incubated with 1% octylglucoside at 37° C. for 30 minutes rather than in SDS.

Results:

Results of the sera blotting experiments are shown in Table 1. It should be noted that sera blotting determines the presence in patients of antibodies specific against a given antigen, and so when a patient has previously been infected by a pathogen and developed an immune response against an antigen, that immune response may still be detectable at a later date when the patient is no longer infected. Hence background results must be interpreted in light of the general infection of a population by the pathogen. For example, the general population has an infection rate by adulthood of approximately 10% for *C. pneumoniae*, thus a background rate of detection of *C. pneumoniae* antigens of up to 10% should be expected.

Conclusions:

The sera from Group A children did not recognise *C. pneumoniae* on immunoblot. The Group B sera from children with evidence of *C. pneumoniae* infection recognised a range of antigens with apparent molecular weights ranging from 30 to 180 kDa. IgM for an antigen complex at 60/62 kDa which occurred as a doublet was immunodominant as well as an antigen at 51 kDa. For IgG the antibody was most pronounced for the antigen at 51 kDa. In the cardiac patients, 23 produced antibody and this was for IgM against the bands at 67, 60/62 and 51 kDa. For IgG this was the band at 51 kDa. For Group D IgM was most pronounced for the 60/62 kDa doublet and IgG for the band at 180 kDa and the doublet at 60/62 kDa. This group of sera contains those with infection most likely due to *Chlamydia psittaci*. The sera from Group E patients infected with *Chlamydia trachomatis* did not cross-react.

Group F Sera

On re-blotting with those sera previously positive for the 60/62 kDa doublet and 51 kDa, the doublet disappeared whilst the band at 51 kDa remained. This showed that the band at 51 kDa was stable to and released by octylglucoside treatment.

Solubility in Octylglucoside

Using samples from Group F patients, separation of antigens from elementary bodies using 1-D gel electrophoresis and SDS gave a different staining pattern compared to using 1-D gel electrophoresis and octylglucoside. The 51 kDa band was still visible after octylglucoside. The pair of antigenic bands at 60/62 kDa was not visible in octylglucoside. Therefore a distinguishing character of the 51 kDa antigen of the present invention is its solubility in octylglucoside.

N-Terminal Amino Acid Sequencing

N-Terminal amino-acid sequencing was performed upon the 51 kDa band. The resulting sequence was then used to query the *Chlamydia* Genome Project database which identified the protein of SEQ ID NO: 2 and a *C. trachomatis* homologue.

Epitope Mapping

A series of overlapping peptides of 15 amino acids covering the derived amino acid sequence of the protein were synthesised on polyethylene pins with reagents from an epitope scanning kit (Cambridge Research Biochemicals, Cambridge, UK) as described previously by Geysen et al. (1987, Journal of Immunological Methods, 102: 259–274). Peptide 1 consisted of residues 1 to 15, peptide 2 consisted of residues 2 to 16 etc. The reactivity of each peptide with patient sera (diluted 1:200) was determined for IgG by ELISA. Data were expressed as A405 after 30 minutes of incubation.

Sera from patients as follows:

Group 1: Children with respiratory tract infection and no evidence of *Chlamydia pneumoniae* as shown by negative immunoblot and microimmunofluorescence (less than 1 in 64) (n=3).

Group 2: Children with respiratory tract infection, positive immunoblot and microimmunofluorescence test greater than 1 in 512 (n=6).

Group 3: Patients undergoing cardiac surgery for advanced coronary disease and antibody on immunoblot (n=2).

Group 4: Patients presenting with history of chest pain, negative troponin (<0.2), negative immunoblot (n=3).

Group 5: Patients presenting with early coronary, positive troponin (>0.2) and antibody on immunoblot (n=8).

Results

Epitope Mapping

Epitope mapping defined eleven areas where children with acute chlamydial infection produced wells with a mean optical density (OD) greater than 1. In the case of epitopes having SEQ ID NOs: 4, 5, 6, 7, 8, 10, 12 and 14 the mean OD was at least 2 standard deviations above that of Group 1 (children with no evidence of *C. pneumoniae* infections). This applied also to Groups 3, 4 and 5 with the exception of SEQ ID NO: 5 which was positive in Groups 4 and 5.

Peptide 1(SEQ ID NO: 15) representing epitope having the sequence of (i.e. which is carried by the peptides having the sequence of) SEQ ID NO: 8 and peptide 2 (SEQ ID NO: 16) representing the carboxy end of SEQ ID NO: 4, the epitope having the sequence of SEQ ID NO: 5 and the amino end of SEQ ID NO: 6 were synthesised.

Preparation of Rabbit Polyclonal Serum

New Zealand white rabbits were pre-bled and then immunised subcutaneously with either peptide 1 or peptide 2 (0.1 ml of 1 mg/ml) conjugated to KLH suspended in either Freund's adjuvant (injection at day 0) or Freund's incomplete adjuvant on days 14, 42, and 70). Serum was obtained for indirect ELISA at the terminal bleed-out.

Indirect ELISA

By a simple adsorption of each peptide to a microtitre plate the following procedure was performed The peptide was dissolved in 2 ml of 0.01 M phosphate buffer saline (PBS), pH 7.2 and diluted to a concentration of 10 µg/ml (1/100) in the same buffer.

1. 150 µl aliquots of peptide (10 µg/ml in 0.01 M PBS) were pipetted into the wells of a Falcon 3912 microassay plate and were incubated overnight at 4° C.
2. The unbound peptide was removed by washing four times (4×10 minutes) with 0.05% Tween 20 in 0.01 M PBS (pH 7.2).
3. The plates were blocked with 2% skimmed milk-10% FCS in 0.01 M PBS for 1 hour at 37° C.
4. The plates were washed four times (4×10 minutes) with 0.05% Tween 20 in 0.01 M PBS and the serum under investigation was added (1/100 dilution in blocking solution) into the wells of micro assay plate (three wells used for each serum) and incubated for 2 hours at 37° C.
5. The plates were washed four times (4×10 minutes) with 0.05% Tween 20 in 0.01 M PBS and secondary antibody, anti-rabbit IgG peroxidase conjugate (1/1000 dilution in blocking solution) was added and incubation proceeded for 1 hour at 37° C.
6. The plates were washed four times (4×10 minutes) with 0.05% Tween 20 in 0.01 M PBS, followed by a further washing with 0.01 M PBS. The plate was then incubated for 45 minutes at room temperature with agitation in 0.5 mg/ml of freshly prepared 2,2 Azino-bis[3-ethylbenz-thiazoline-6-sulfonic acid]diammonium (ABTS tablets) in pH 4.0 citrate buffer with 0.01% (w/v) hydrogen peroxide.
7. Optical density (OD) measurements were made with an ELISA plate reader (Titertek Miltiscan) at a wavelength of 405 nm.
8. The average readings for each three wells for each serum was determined.

Results

The results shown in Table 3 demonstrate seroconversion to each individual peptide.

Expression of the Amino-end of the Protein

The sequence was codon optimised (Genosys, Calif.) for E.coli and a BamHI and Not1 site added to opposite ends. The optimised sequence and PET 29 vector (Novagen, Wis.) were restriction digested using BamHI and Not1 and transformed by heat shock into E. coli strain BL21 (Invitrogen, Carlsbad, Calif.). The expressed amino acids were from amino acids 1–292 and included the epitopes represented by peptides 1 and 2. This construct included an S-tag and Thrombin cleavage site at the amino end and histidine tag at the carboxy end (SEQ ID NO: 3).

Purification

The transformants were expressed as follows. Briefly, 5 ml of an overnight culture was used to inoculate 500 ml LB (50 µg/ml kanamycin, 34 µg/ml chloramphenicol) which was grown for 2 hours at 37° C. to an OD 600 of 0.5, then induced for 3 hours with 0.1 mM IPTG (Sigma, Poole Dorset). The cells were pelleted and disrupted by crushing at −20° C. in an XPRESS. The buffer (50 mm $NaH_2PO_4$, 0.5 M NaCl, 10 mm imidazole) and the cell debris pelleted down. The supernatant was filter sterilised and put on a Ni-NTA agarose slurry affinity column (Qiagen) in order to capture the His-tagged recombinant protein. The column was washed 3 times with 4 ml of washing buffer and the protein eluted maximally with 150 mM imidazole. The protein gave a single band on a 10% acrylamide gel stained with Coomassie Brilliant Blue with an apparent molecular weight of 37 kDa. On Western blot counterstaining with the anti-His mouse alkaline phosphate conjugate (1:2,500) (Sigma, Dorset, Poole) this produced a single band at 37 kDa and a breakdown product at 35 kDa. The protein concentration of the elute was measured and standardised to 10 mg/ml.

Amino Acid Sequencing

The protein was amino end cleared to remove the S-tag using a Thrombin cleavage Kit (Novagen). The digestion reaction was 5 µl 10× Thrombin cleavage buffer, 0.5 mg purified recombinant protein, 1 µl of 0.01 µg/ml Thrombin which was left at room temperature for 18 hours. The reaction mix was run on a 12% SDS-PAGE gel and transferred onto PVDF membrane (Amersham, Chalfont, UK). This was stained with Coomassie Brilliant Blue and the protein bands destained and excised. Direct amino acid sequencing gave amino acids 28–32 of SEQ ID NO: 3 which matched the amino end (Department of Biochemistry, University of Cambridge).

Human Recombinant Antibodies

These peptides and the purified recombinant proteins were used to pan the phage display library. The peptide and recombinant protein were used at 10 mg/ml on NunC immunotubes Bst-N1 fingerprints of the PCR-amplified ScFv inserts before panning showed a highly heterogeneous library. After panning against peptide 1, 7 fingerprints were identified of which four were represented by more than one clone (A, B, C, D). These were combined as a pool for a neutralisation assay (pool 1) (below). After panning against peptide 2, clone A was present as well as a new ScFv, E. A and E were combined to produce pool 2. Against the clone recombinant fragment ScFvs E, F and G were present as well as a further ScFv, H. ScFvs E, F, G and H were tested together as pool 3.

Neutralisation Assays

Chang cells (50 ml of $10^6$ cells/ml) in maintenance media were grown overnight at 37° C. with 5% $CO_2$. Chang cells (1 ml of 1×$10^6$ cells/ml maintenance media) were grown overnight at 37° C. with 5% $CO_2$ in plastic bijoux containing a thin glass circle on which the cells can grow. For recombinant protein or peptide assay (0.1 µl/ml), 100 µl of each sample was incubated with shaking for 1 hour with the cells at 37° C. For the phage and sera assays, 100 µl of each sample (1:10 rabbit sera or dialysed phage pools 1–3) were incubated with 100 µl elementary bodies (EB) for 1 hour at 37° C., shaking. After this first incubation, the 100 µl EB or 200 ml of the phage or rabbit sera/EB mix was added to the Chang cells. This was incubated with shaking for 1 hour at 37° C. The supernatant was removed from every sample and replaced by 1 ml of fresh maintenance media. This was incubated at 37° C. with 5% $CO_2$ for 72 hours.

For both assays, the inclusion bodies were fixed and stained the following way; the cells were washed twice with PBS, then fixed with 100% methylated spirits for 10 minutes and washed twice again with PBS. The glass circles were incubated for 30 minutes with 10 μl of mouse *C. pneumoniae* inclusion bodies monoclonals (Mab) then washed 3 times with PBS and incubated for 30 minutes with 100 μl of fluorescein conjugated anti-mouse IgG. The inclusion bodies were then observed by fluorescence microscopy and three 200× fields counted. EB only samples were used as a positive control for chlamydial infection and dialysed phage supernatant without EB as a negative control.

Results

See Table 4 (Table of Neutralisation Assays).

Conclusion

Pre-incubation with the rabbit antiserum against peptide 2 and peptide 2 itself reduced the infectivity due to *C. pneumoniae*. Incubation with peptide 1 produced a similar reduction. The pools of phages were also active.

Overall this demonstrated the immunogenicity of the antigen the potential therapeutic effect of peptides representing its key epitopes and both rabbit hyperimmune antiserum and ScFvs against these epitopes.

TABLE 1

| Apparent Molecular Weight (kDa) | Group B (N = 18) | | Group C (N = 18) | | Group D (N = 27) | | Group E (N = 21) | |
|---|---|---|---|---|---|---|---|---|
| | IgM | IgG | IgM | IgG | IgM | IgG | IgM | IgC |
| 180 | | 1 | | 2 | | 2 | 1 | 6 | 1 |
| 130 | | | 2 | | | 1 | 4 | | |
| 120 | 1 | | 5 | | 1 | 1 | 5 | | 1 |
| 98 | | | 5 | | | 1 | 2 | 5 | 2 |
| 90 | | | 2 | | | | 2 | | |
| 67 | | | 2 | 5 | 1 | | | 1 | 1 |
| 60/62* | 8 | | 5 | 5 | | 13 | 7 | 2 | 2 |
| 51 | 7 | 11 | 9 | 10 | 2 | 3 | 1 | 2 |
| 47 | 1 | 1 | 1 | | 0 | 0 | 0 | 0 |
| 40 | 0 | 0 | 0 | 3 | 0 | 0 | 0 | 1 |
| 30 | | 4 | 0 | 3 | | 2 | | 2 |

*runs as a doublet within 1 mm of each other

TABLE 2

| | | Value for[a] | | | | |
|---|---|---|---|---|---|---|
| Well No. | Epitope SEQ ID NO | Group 1 (n = 3) | Group 2 (n = 6) | Group 3 (n = 2) | Group 4 (n = 3) | Group 5 (n = 8) |
| 3 | 9 | 0.538 ± 0.205 | 1.028 ± 0.423 | 0.425 ± 0.036 | 0.416 ± 0.184 | 0.499 ± 0.191 |
| 4 | | 0.599 ± 0.252 | 1.487 ± 0.462 | 0.502 ± 0.036 | 0.407 ± 0.107 | 0.438 ± 0.162 |
| 13 | 10 | 0.462 ± 0.203 | 1.103 ± 0.229 | 0.473 ± 0.026 | 0.421 ± 0.162 | 0.427 ± 0.188 |
| 31 | 11 | 0.491 ± 0.192 | 1.103 ± 0.310 | 0.440 ± 0.004 | 0.407 ± 0.105 | 0.310 ± 0.129 |
| 41 | 12 | 0.547 ± 0.235 | 1.169 ± 0.256 | 0.474 ± 0.024 | 0.393 ± 0.08 | 0.376 ± 0.158 |
| 43 | 13 | 0.598 ± 0.258 | 1.223 ± 0.323 | 0.558 ± 0.015 | 0.423 ± 0.119 | 0.406 ± 0.181 |
| 55 | 4 | 0.547 ± 0.235 | 1.265 ± 0.334 | 0.475 ± 0.02 | 0.373 ± 0.076 | 0.381 ± 0.042 |
| 58 | 5 | 0.611 ± 0.019 | 1.025 ± 0.06 | 0.611 ± 0.019 | 1.127 ± 0.253 | 0.800 ± 1.232 |
| 59 | 6 | 0.494 ± 0.166 | 1.096 ± 0.267 | 0.547 ± 0.009 | 0.546 ± 0.200 | 0.702 ± 0.144 |
| 60 | 7 | 0.489 ± 0.129 | 1.048 ± 0.270 | 0.483 ± 0.064 | 0.388 ± 0.008 | 0.449 ± 0.140 |
| 61 | | 0.530 ± 0.236 | 1.051 ± 0.262 | 0.59 ± 0.089 | 0.446 ± 0.09 | 0.784 ± 0.257 |
| 76 | 8 | 0.485 ± 0.158 | 1.174 ± 0.255 | 0.654 ± 0.068 | 0.564 ± 0.223 | 0.666 ± 0.266 |
| 79 | 14 | 0.510 ± 0.235 | 1.21 ± 0.273 | 0.418 ± 0.003 | 0.423 ± 0.127 | 0.388 ± 0.153 |

[a]Optical density ± Standard deviation

TABLE 3

| | [a]Pre Serum | Post Serum |
|---|---|---|
| Peptide 1 | 0.055 ± 0.01 | 0.591 ± 0.06 |
| Peptide 2 | 0.056 ± 0.01 | 0.507 ± 0.04 |

[a]optical density ± standard derivation

TABLE 4

Table of Neutralisation Assays

| | Number of Elementary Bodies in Three 200x Fields |
|---|---|
| Cell control (dialysed phage supernatant) | 0 |
| Cell control (elementary bodies) | 30 |
| Rabbit anti-serum | |
| Versus peptide 1 | 30 |
| Versus peptide 2 | 19 |
| Pre-incubation | |
| Peptide 1 | 13 |
| Peptide 2 | 0 |
| Recombinant protein | 12 |
| Phage Pools | |
| Pool 1 | 18 |
| Pool 2 | N/D |
| Pool 3 | 21 |

What is claimed is:

1. An isolated polypeptide consisting of the amino acid sequence as set forth in SEQ ID No:16.

2. A composition comprising an isolated polypeptide according to claim 1 and a pharmaceutically acceptable carrier, diluent or excipient.

* * * * *